(12) United States Patent
Birk (10) Patent No.: US 6,503,264 B1
(45) Date of Patent: Jan. 7, 2003

(54) ENDOSCOPIC DEVICE FOR REMOVING AN INTRAGASTRIC BALLOON

(75) Inventor: Janel Birk, Oxnard, CA (US)

(73) Assignee: BioEnterics Corporation, Carpinteria, CA (US)

( * ) Notice: Subject to any disclaimer, the term of this patent is extended or adjusted under 35 U.S.C. 154(b) by 0 days.

(21) Appl. No.: 09/518,505

(22) Filed: Mar. 3, 2000

(51) Int. Cl.[7] .............................................. A61M 29/00
(52) U.S. Cl. ....................................... 606/191; 606/139
(58) Field of Search ................................ 606/139, 140, 606/141, 142, 144, 147, 148, 191, 192, 205, 206, 207, 193, 195, 110, 113, 126; 600/104

(56) References Cited

U.S. PATENT DOCUMENTS

| 4,246,893 A | 1/1981 | Berson |
| 4,416,267 A | 11/1983 | Garren et al. |
| 4,723,547 A | 2/1988 | Kullas et al. |
| 4,899,747 A | 2/1990 | Garren et al. |
| 4,930,535 A | 6/1990 | Rinehold |
| 5,084,061 A | 1/1992 | Gau et al. |
| 5,234,454 A | 8/1993 | Bangs |
| 5,259,399 A | 11/1993 | Brown |
| 5,401,241 A | 3/1995 | Delany |
| 5,817,111 A | * 10/1998 | Riza ............................ 606/148 |
| 5,843,028 A | 12/1998 | Weaver et al. |
| 5,868,141 A | 2/1999 | Ellias |
| 5,921,915 A | * 7/1999 | Aznoian et al. ............. 606/104 |

* cited by examiner

Primary Examiner—Kevin T. Truong
Assistant Examiner—Vy Q. Bui
(74) Attorney, Agent, or Firm—Milbank, Tweed, Hadley & McCloy LLP (57) ABSTRACT

A device and method for removing a fluid-filled object from a body cavity of a patient is provided. The device includes a tube and a grasper slidably movable with respect to the tube. The device also includes a needle fixed to one end of the tube.

In use, the device is inserted into the body cavity, and the object is punctured with the needle. The object is grasped by the grasper, and the object and the device are removed from the body cavity.

18 Claims, 7 Drawing Sheets

ENDOSCOPIC DEVICE FOR REMOVING AN INTRAGASTRIC BALLOON

BACKGROUND

1. Field of the Invention

The present invention relates to endoscopic devices for removing an intragastric fluid-filled object from the stomach of a patient.

2. Description of the Related Art

Intragastric balloons, such as that described in U.S. Pat. No. 5,084,061, or commercially available as the BioEnterics Intragastric Balloon System (sold under the trademark BIB), are designed to provide short-term therapy for moderately obese individuals who need to shed pounds in preparation for surgery, or as part of a dietary and behavioral modification program.

The BIB system, for example, consists of a silicone elastomer intragastric balloon which is inserted into the stomach and filled with fluid. Commercially available intragastric balloons are filled with saline solution or air. The intragastric balloon functions by filling the stomach and enhancing appetite control. Placement of the intragastric balloon is non-surgical, usually requiring no more than 20–30 minutes. The procedure is performed endoscopically in an outpatient setting, using local anesthesia and sedation. Placement is temporary, and intragastric balloons are typically removed after six to twelve months.

Historically, endoscopic deflation and extraction of intragastric balloons has been an arduous task due to the difficulty associated with manipulating the balloon within the stomach. Due to the balloon's flexible nature, when pressure is applied to its surface for puncture, the shell will either elastically deform or the entire balloon will push away from the applied force.

The prior art method of removing the balloon involves several steps, each with its own tool. A sharp-ended puncture device, sometimes called a "killer," is inserted through the working channel of an endoscope to puncture the balloon. The puncture device is removed, and the saline solution is either allowed to enter the stomach cavity, or removed via a tube inserted through the working channel and into the balloon. Finally, a grasping device or "grasper" having prongs, teeth, or a wire loop is inserted through the working channel to snag or snare the balloon and is used to pull the balloon through the esophagus or the working channel. Heretofore, there has been no single instrument capable of being inserted down the working channel of a endoscope which will (1) pierce the balloon, (2) evacuate the fluid and deflate the balloon, (3) grasp the balloon, and (4) allow the deflated balloon to be withdrawn.

Therefore, it is desirable to provide an endoscopic device for removing an intragastric balloon in which the above mentioned disadvantages are substantially overcome.

SUMMARY OF THE INVENTION

A device and method for evacuating and removing a fluid-filled object from a body cavity of a patient is provided. The device includes a tube and a grasper slidably movable with respect to the tube. The device also includes a needle fixed to one end of the tube.

In use, the device is inserted into the body cavity, and the object is punctured with the needle. The object is grasped by the grasper, and the object and the device are removed from the body cavity.

DETAILED DESCRIPTION OF THE DRAWINGS

FIGS. 1–9 depict embodiments of the invention, each of which is a single device that can puncture the balloon, grasp the balloon, evacuate the saline solution, and extract the device through the esophagus. FIGS. 1–6 depict a device 100, 200 constructed of dual lumen tubing 10, 20 that is small enough to pass through the working channel of an endoscope or gastroscope (not shown). One lumen 11, 21 has a cannulated needle 12, 22 fluidly coupled at one end of lumen 11, 21 for puncturing and suctioning out the saline solution. The other end of lumen 11, 21 is fluidly coupled by tubing 13 to luer connector 14 for connection to suction in the operating room or clinical office. The other lumen 15, 25 houses a grasper 16, having prongs 17, which is free to slide within lumen 15, 25.

When the balloon (not shown) full of fluid is ready for removal, the device 100, 200 is guided down the working channel (not shown) of an endoscope or gastroscope (not shown). The needle 12, 22 will be used to puncture and steady the balloon while the grasper 16, 26 is used to grasp the taut shell of the balloon. After the grasper 16 has grasped the balloon by snagging the balloon with the prongs 17, the grasper 16 is retracted into the lumen 15, 25 to maintain a firm grasp of the balloon. Suction will then be applied to the luer connector 14 and thus to lumen 11, 21 and needle 12, 22 to evacuate the fluid. After all of the fluid is evacuated from the balloon, the entire device 100, 200 with the balloon attached is pulled up through the esophagus. It is anticipated that this mechanism will introduce ease of use, reliability, and could be produced at a reasonably low cost.

FIGS. 1, 2, 3A, 3B, and 4 depict aspects of a crescent-form embodiment of the device 100, which is a preferred embodiment of the invention. FIGS. 4, 5, 6A, 6B, and 7 depict aspects of a D-form embodiment of the device 200, which is another preferred embodiment of the invention. The purpose for these two variations is to maximize the cross-sectional area of one lumen in the dual-lumen tubing.

In the crescent-form variation of the device 100, tubing 10 has a lumen 11 having a crescent-shaped cross-section, which occupies the portion of tubing 10 not occupied by either lumen 15, having a circular cross-section, or separating wall 18. In this embodiment, needle 12 has a crescent-shaped cross-section for fluid-tight insertion into lumen 11.

Similarly, in the D-form device 200, tubing 20 has a lumen 21 having a D-shaped cross-section, which occupies the portion of tubing 20 not occupied by either lumen 25, having a circular cross-section, or separating wall 28. In this embodiment, needle 22 has a D-shaped cross-section for fluid tight insertion into lumen 21.

Figure 1:
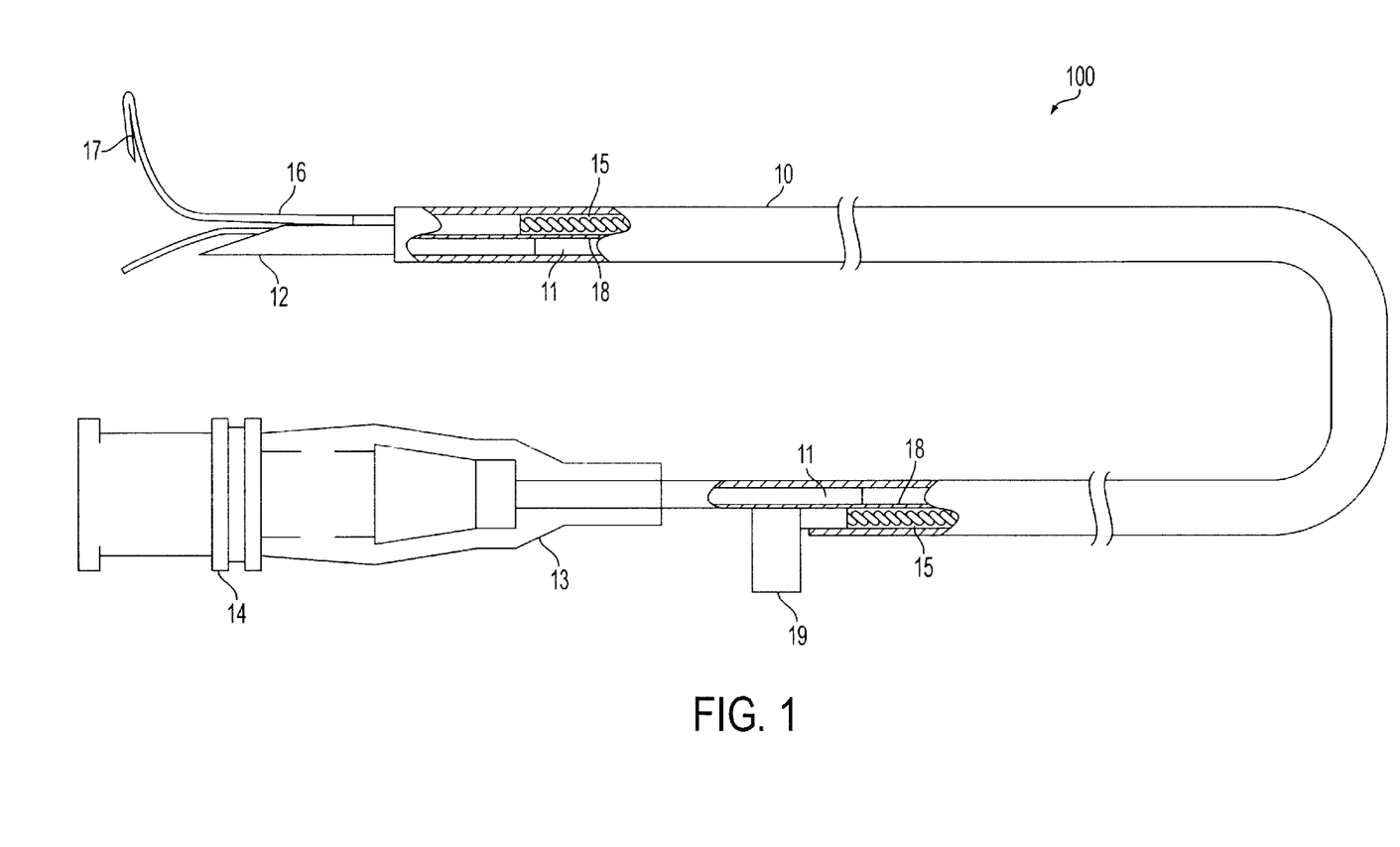
FIG. 1 is a schematic view which illustrates a crescent-form embodiment of the invention.
Figure 2:
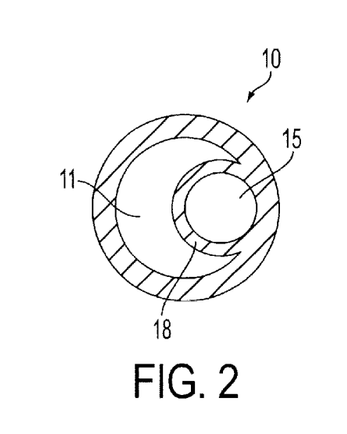
FIG. 2 is a longitudinal cross-sectional view of a crescent-form tube embodying aspects of the invention.
Figure 3A:
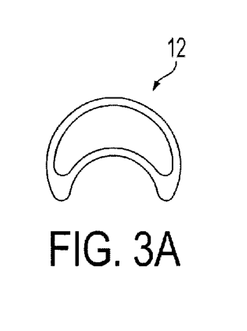
FIGS. 3A and 3B are, respectively, longitudinal and lateral cross-sectional views of a crescent-form cannulated needle embodying aspects of the invention.
Figure 3B:
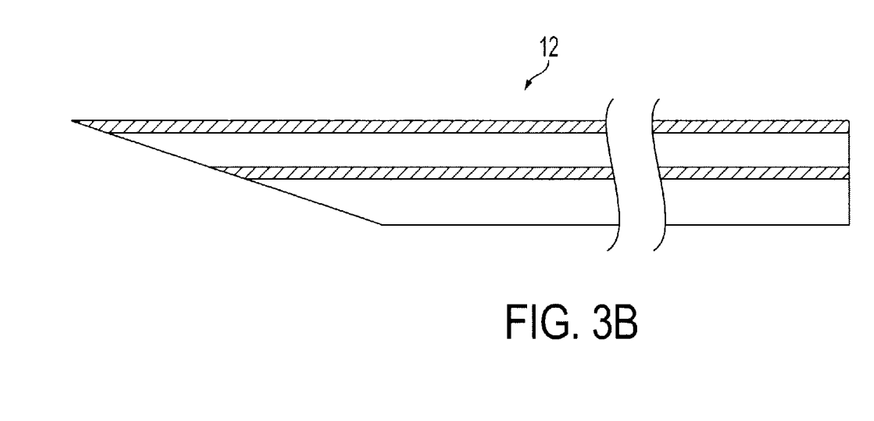
Figure 4:
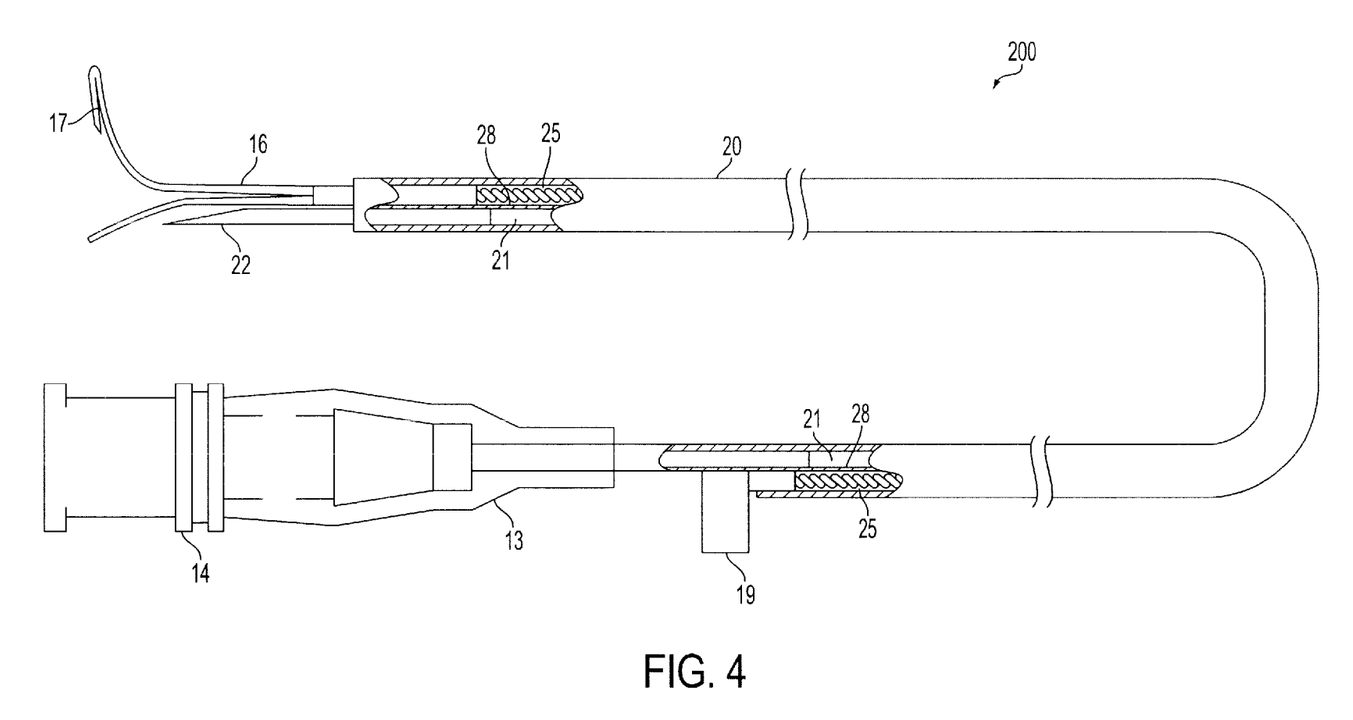
FIG. 4 is a schematic view which illustrates a D-form embodiment of the invention.
Figure 5:
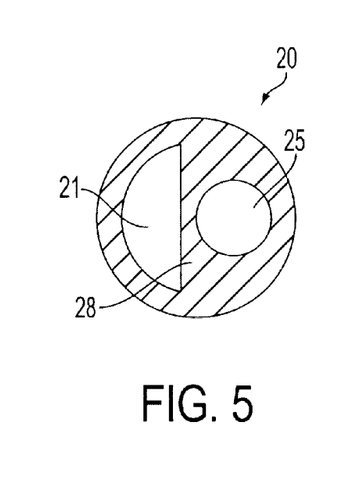
FIG. 5 is a longitudinal cross-sectional view of a D-form tube embodying aspects of the invention.
Figure 6A:
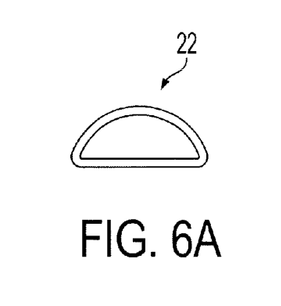
FIGS. 6A and 6B are, respectively, longitudinal cross-sectional and lateral views of a D-form cannulated needle embodying aspects of the invention.
Figure 6B:
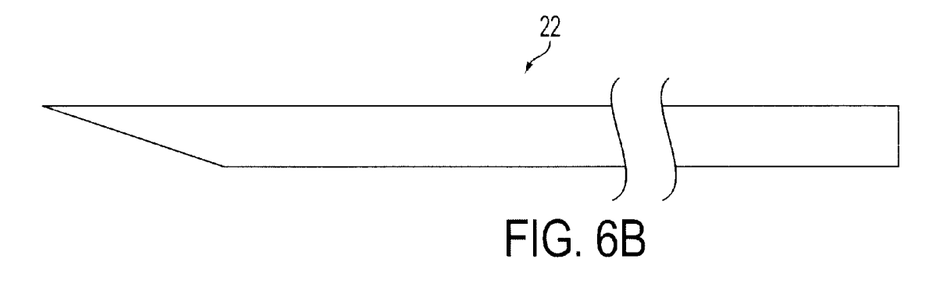
Figure 7A:
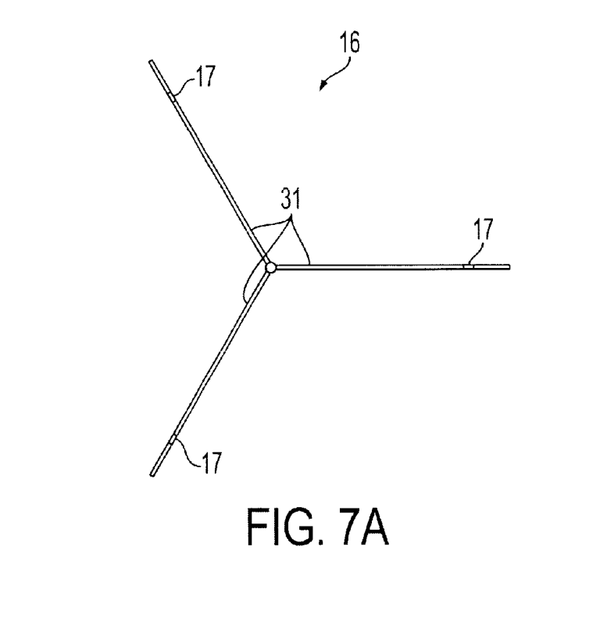
FIGS. 7A and 7B are, respectively, longitudinal and lateral views of a wire grasper embodying aspects of the invention.
Figure 7B:
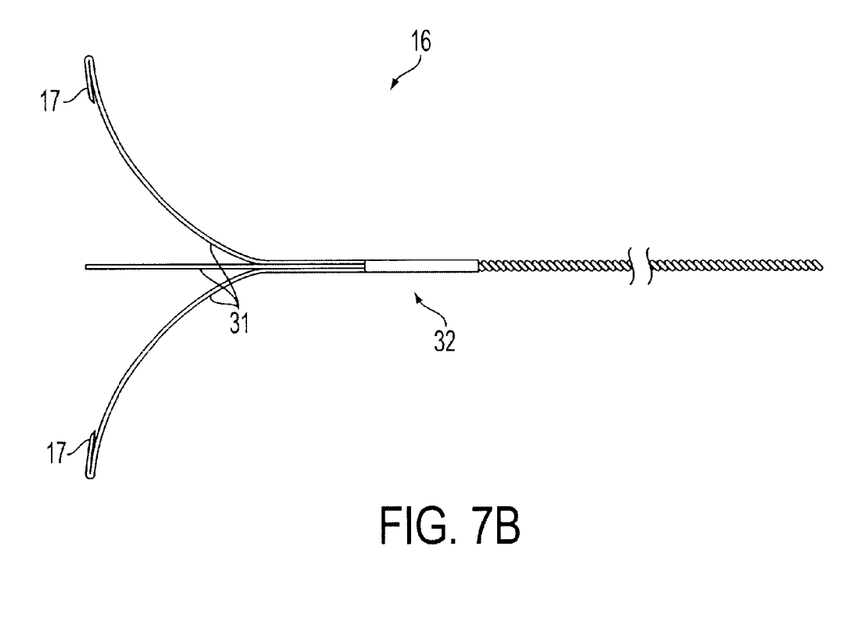

In preferred embodiment of the invention, tubing 10, 20 may be fabricated from PTFE, ETFE, or PDVF, and may have a 0.100" (2.540 mm) outer diameter; circular lumen 15, 25 may have a 0.038" (0.965 mm) interior diameter. Needle 12, 22 preferably has the form shown in either FIGS. 3A, 3B or 6A, 6B, and preferably is fabricated from 304 stainless steel, and may be fixed in place within lumen 11, 21 using LOCTITE® 3201 UV cure adhesive. FIGS. 7A, 7B show a preferred embodiment of the grasper 16 of the invention, which is formed of three strands of 0.012" (3.048 mm) diameter 304 stainless steel wire 31 joined by solder connection 32. Grasper 16 preferably has a handle 19 for manipulation by the operator.

Figures 8A, 8B:
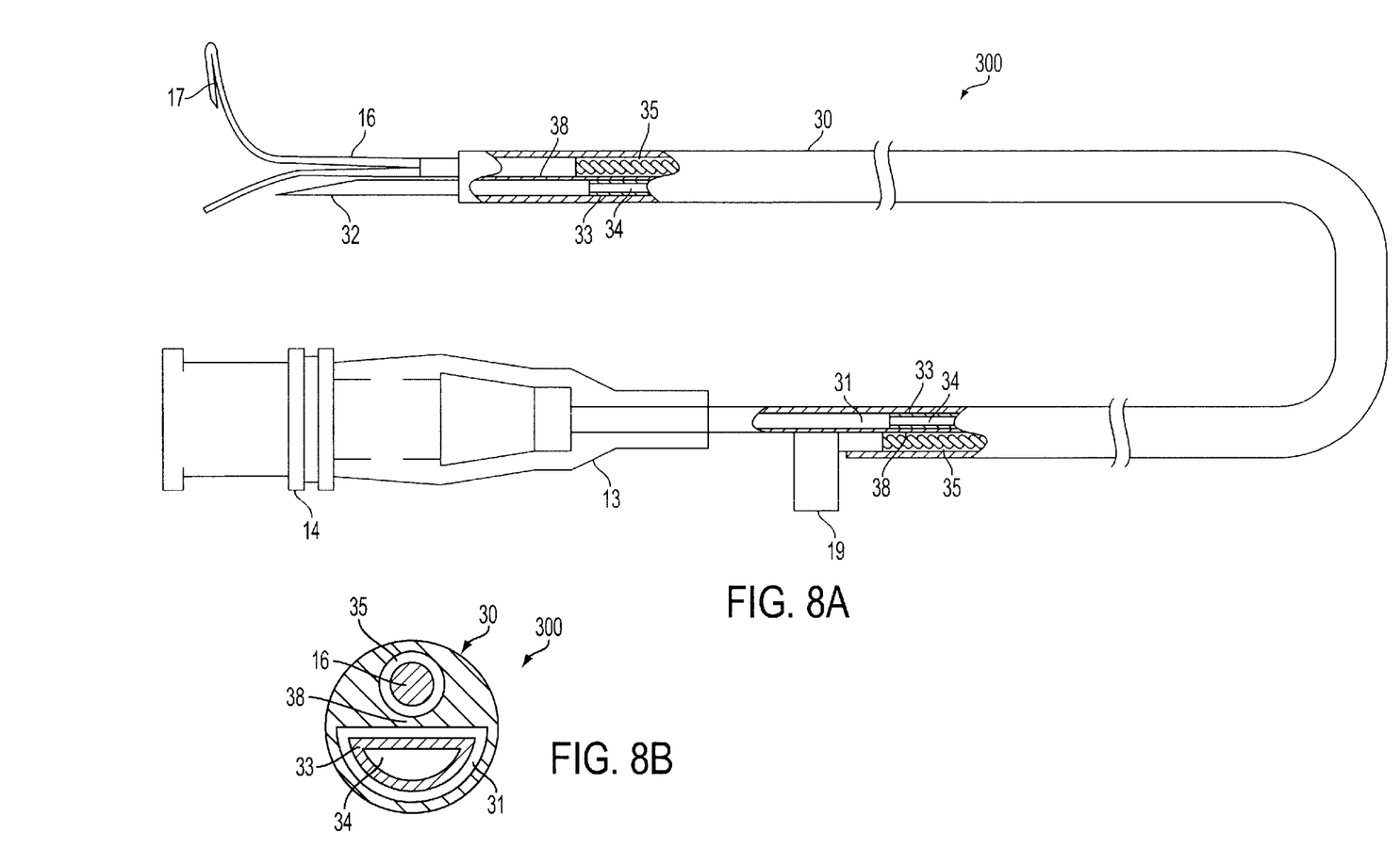
FIGS. 8A and 8B are, respectively, longitudinal cross-sectional and schematic views which illustrate a nested-tube embodiment of the invention having a dual-lumen outer tube.
Figures 9A, 9B:
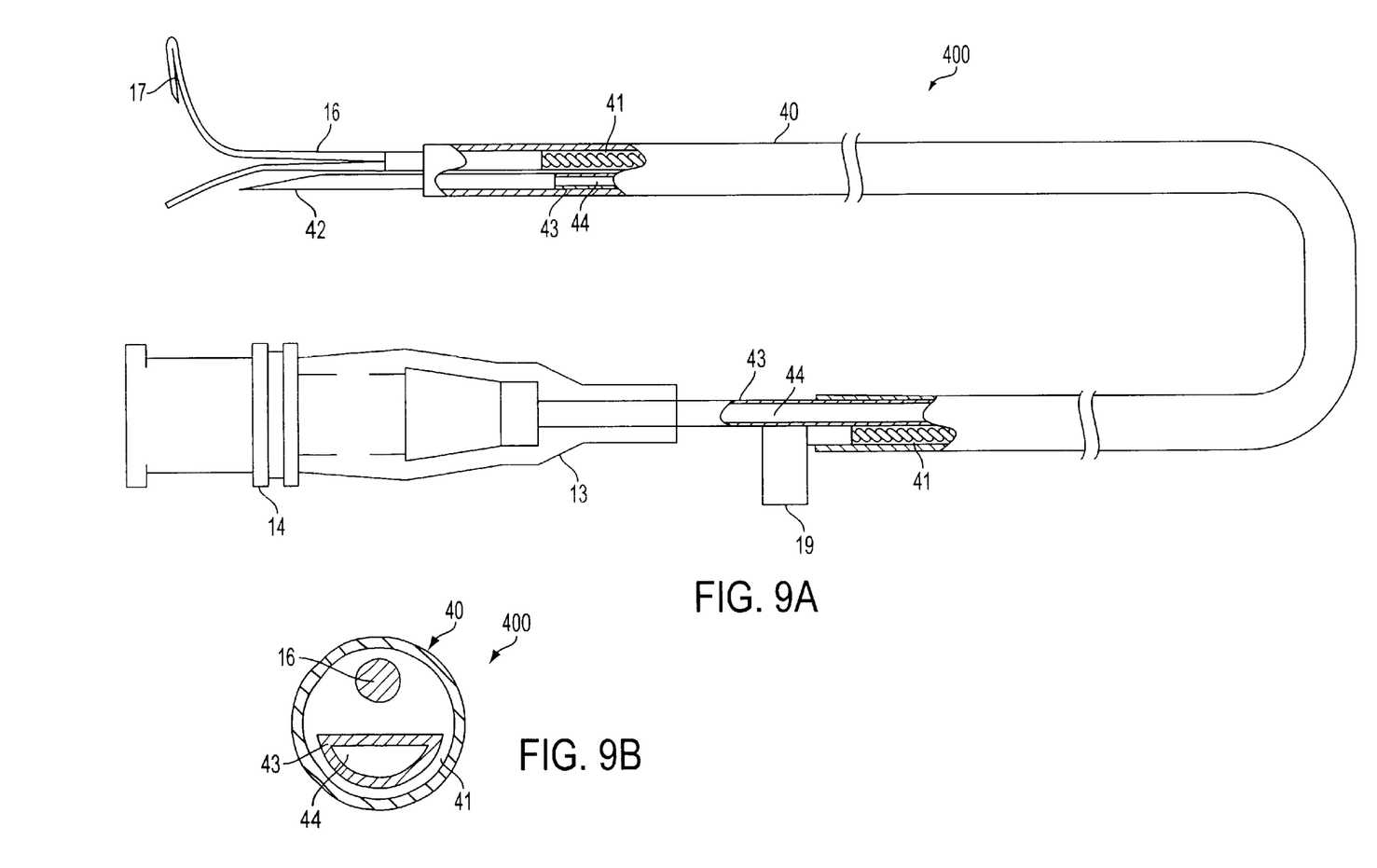
FIGS. 9A and 9B are, respectively, longitudinal cross-sectional and schematic views which illustrate a nested-tube embodiment of the invention having a single-lumen outer tube.

FIGS. 8 and 9 depict nested-tube embodiments of the invention. The device 300, 400 is constructed of an outer tube 30, 40 that is small enough to pass through the working channel of an endoscope or gastroscope (not shown). An inner tube 33, 43 and cannulated needle 32, 42 are fluidly coupled and are slidably movable within a lumen 31, 41 of outer tube 30, 40. Lumen 34, 44 of inner tube 33, 43 is also fluidly coupled to luer connector 14. Outer tube 30, 40 also houses a grasper 16 which is free to slide within lumen 35, 45 of outer tube 30, 40. In these embodiments, cannulated needle 32, 42 may be completely retracted within outer tube 30, 40 to prevent injury to the patient's esophagus or the working channel of the endoscope when the device 300, 400 is removed.

FIGS. 8A and 8B show a nested-tube embodiment as described above where dual-lumen outer tube 30 has a lumen 31 having a D-shaped cross-section, which occupies the portion of tube 30 not occupied by either lumen 35, having circular cross-section, or separating wall 38. In this embodiment, cannulated needle 32 and inner tube 33 have a D-shaped cross-section with dimensions appropriate to allow sliding movement within outer tube lumen 31. By contrast FIGS. 9A and 9B show a nested-tube embodiment where outer tube 40 has a single lumen 41, in which both inner tube 43, having D-shaped cross section, and grasper 16 are slidably movable.

In another embodiment of the invention, grasper 16 may have teeth rather than prongs, or may be a loop or snare. A longer or smaller number of prongs may be used than the embodiments illustrated in FIGS. 1–9.

In further embodiments of the invention, the cannulated needle may have circular or other cross sections.

In still further embodiments of the invention, a cannulated needle may be fluidly coupled to a single-lumen tube, inside which a grasper is slidably movable. In use, the punctured and evacuated balloon is grasped and pulled into the cannulated needle.

It is to be understood that the above-described embodiments are merely illustrative of the principles of the invention and that other arrangements may be devised by those skilled in the art without departing from the spirit and scope of the invention.

I claim:

1. A device for removing an object from a body cavity of a patient comprising:
   a first tube;
   a grasper slidably movable with respect to said first tube, said grasper having an end having at least one prong, said prong having a sharp tip; and
   a needle fixed to an end of said first tube.

2. The device of claim 1 wherein said first tube has a first lumen and a second lumen, said grasper slidably movable in said first lumen.

3. The device of claim 1 wherein said device has an outer diameter suitable for insertion within a working channel of an endoscope.

4. The device of claim 1 wherein said needle is cannulated and fluidly coupled to said end of said first tube.

5. The device of claim 4 wherein said first tube has a first lumen and a second lumen, said needle fluidly coupled to said second lumen.

6. The device of claim 1 further comprising a second tube, said first tube slidably movable in said second tube and said grasper slidably movable in said second tube.

7. A device for removing an object from a body cavity of a patient comprising:
   a first tube;
   a grasper slidably movable with respect to said first tube; and
   a needle fixed to an end of said first tube;
   a second tube, said first tube slidably movable in said second tube and said grasper slidably movable in said second tube, said second tube having a first lumen and a second lumen, said grasper slidably movable in said first lumen and said first tube slidably movable in said second lumen.

8. A method for evacuating and removing a fluid-filled object from a body cavity of a patient comprising the steps of:
   inserting a device into the body cavity, said device having
      a first tube,
      a grasper slidably movable with respect to said first tube, said grasper having an end having at least one prong, said prong having a sharp tip, and
      a needle fixed to a distal end of said tube;
   puncturing the object with said needle;
   grasping the object with said grasper; and
   removing the object and said device from the body cavity.

9. The method of claim 8 wherein said needle is cannulated and fluidly coupled to said distal end of said first tube, and further comprising the step of evacuating at least some fluid from the object through said needle and said first tube.

10. A method for evacuating and removing a fluid-filled object from a body cavity of a patient comprising the steps of:
   inserting a device into the body cavity, said device having a first tube, a grasper slidably movable with respect to said first tube, and a needle fixed to a distal end of said tube;
   said needle is cannulated and fluidly coupled to said distal end of said first tube,
   puncturing the object with said needle;
   grasping the object with said grasper;
   removing the object and said device from the body cavity;
   evacuating at least some fluid from the object through said needle and said first tube; and applying suction to a proximal end of said first tube so that fluid is evacuated from the object by said suction through said distal end of said first tube.

11. The method of claim 8, said first tube further having a first lumen and a second lumen, said grasper slidably movable in said first lumen and said needle is cannulated and fluidly coupled to said second lumen.

12. The method of claim 8 wherein said grasping step further comprises the steps of: extending said grasper from a distal end of said device; and retracting said grasper into said distal end of said device.

13. The method of claim 12 wherein said extending step further comprises extending said grasper from a first lumen of said first tube and said retracting step further comprises retracting said grasper into said first lumen of said first tube.

14. The method of claim 13 wherein said needle is cannulated and fluidly coupled to said distal end of said first tube, said extending step further comprises extending said grasper from said needle, and said retracting step further comprising retracting said grasper into said needle.

15. The method of claim 8 further comprising the steps of: inserting said device into the working channel of an endoscope; and removing the object and said device from said endoscope.

16. The method of claim 8 further comprising the steps of:

inserting an endoscope into the body cavity; and removing said endoscope from the body cavity.

17. The method of claim 8 wherein said grasping step further comprises snagging the object with said at least one prong.

18. The method of claim 8 wherein said device further comprises a second tube, said first tube slidably movable in said second tube and said grasper slidably movable in said second tube, and further comprising the step of retracting said needle and said first tube within said second tube.

* * * * *